US006080243A

United States Patent [19]

Insley et al.

[11] Patent Number: 6,080,243

[45] Date of Patent: *Jun. 27, 2000

[54] FLUID GUIDE DEVICE HAVING AN OPEN STRUCTURE SURFACE FOR ATTACHEMENT TO A FLUID TRANSPORT SOURCE

[75] Inventors: Thomas I. Insley, West Lakeland Township; Raymond P. Johnston, Lake Elmo, both of Minn.

[73] Assignee: 3M Innovative Properties Company, St. Paul, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 09/099,565

[22] Filed: Jun. 18, 1998

[51] Int. Cl.[7] ...................................................... A61M 1/00

[52] U.S. Cl. ............................ 134/21; 15/415.1; 15/420; 604/313; 604/317

[58] Field of Search .................................. 15/420, 415.1; 604/313, 317, 902; 134/21

[56] References Cited

U.S. PATENT DOCUMENTS

| | | | |
|---|---|---|---|
| 1,791,760 | 2/1931 | Kline | 15/420 |
| 2,210,030 | 8/1940 | Ellis | 15/420 X |
| 3,520,300 | 7/1970 | Flower, Jr. . | |
| 3,715,192 | 2/1973 | Wenz et al. . | |
| 3,935,863 | 2/1976 | Klinger . | |
| 4,193,156 | 3/1980 | Chauvier | 15/420 X |
| 4,233,029 | 11/1980 | Columbus . | |
| 4,266,581 | 5/1981 | Wenander | 15/413 X |
| 4,271,119 | 6/1981 | Columbus . | |
| 4,277,966 | 7/1981 | Rambauske . | |
| 4,525,166 | 6/1985 | Leclerc . | |
| 4,533,352 | 8/1985 | Van Beek et al. . | |
| 4,668,558 | 5/1987 | Barber . | |
| 4,677,705 | 7/1987 | Schuster . | |
| 4,747,166 | 5/1988 | Kuntz . | |
| 4,809,396 | 3/1989 | Houser . | |
| 4,826,539 | 5/1989 | Harpold . | |
| 4,871,623 | 10/1989 | Hoopman et al. . | |
| 4,906,439 | 3/1990 | Grenner . | |
| 4,921,492 | 5/1990 | Schultz et al. . | |
| 4,950,549 | 8/1990 | Rolando et al. . | |
| 4,966,584 | 10/1990 | Nguyen . | |
| 5,014,389 | 5/1991 | Ogilvie et al. | 15/415.1 X |
| 5,069,403 | 12/1991 | Marentic et al. . | |

(List continued on next page.)

FOREIGN PATENT DOCUMENTS

| | | |
|---|---|---|
| 42 10 072 A1 | 3/1993 | Germany . |
| 1 418 635 | 12/1975 | United Kingdom . |
| WO 89/04628 | 6/1989 | WIPO . |
| WO 99/06589 | 2/1999 | WIPO . |

OTHER PUBLICATIONS

Article: "Fabrication of Novel Three–Dimensional Microstructures by the Anisotropic Etching of (100) and (110) Silicon,"Ernest Bassous, *IEEE Transactions on Electron Devices*. vol. ED–25, No. 10, Oct. 1978.

Article: "Microtechnology Opens Doors to the Universe of Small Space, "Peter Zuska, *Medical Devices & Diagnostic Industry*, Jan. 1997.

*Primary Examiner*—Chris K. Moore

*Attorney, Agent, or Firm*—James A. Rogers

[57] ABSTRACT

A fluid guide device that can evenly and effectively distribute the potential from a fluid transport source over an area substantially larger than the opening of a source conduit. The fluid guide device includes a first major surface having a structured surface that includes a plurality of flow channels disposed thereon. The flow channels extend from a first point to a second point along the structured surface and have a minimum aspect ratio of about 10:1 and a hydraulic radius no greater than about 300 micrometers ($\mu$m). The fluid guide device also includes an active fluid transport source provided external to the structured polymeric surface to provide a potential over the flow channels to promote movement of matter through the flow channels from a first potential to a second potential. The fluid transport source is connected with a plurality of the flow channels of the structured surface by way of a manifold.

18 Claims, 3 Drawing Sheets

U.S. PATENT DOCUMENTS

| | | | |
|---|---|---|---|
| 5,078,925 | 1/1992 | Rolando et al. . | |
| 5,133,516 | 7/1992 | Marentic et al. . | |
| 5,158,557 | 10/1992 | Noreen et al. . | |
| 5,175,030 | 12/1992 | Lu et al. . | |
| 5,200,248 | 4/1993 | Thompson et al. . | |
| 5,249,359 | 10/1993 | Schubert et al. . | |
| 5,437,651 | 8/1995 | Todd et al. . | |
| 5,440,332 | 8/1995 | Good . | |
| 5,450,235 | 9/1995 | Smith et al. . | |
| 5,457,848 | 10/1995 | Miwa . | |
| 5,514,120 | 5/1996 | Johnston et al. . | |
| 5,527,588 | 6/1996 | Camarda et al. . | |
| 5,534,576 | 7/1996 | Grot . | |
| 5,535,478 | 7/1996 | Thompson . | |
| 5,599,330 | 2/1997 | Rainin . | |
| 5,628,735 | 5/1997 | Skow . | |
| 5,651,900 | 7/1997 | Keller et al. . | |
| 5,655,258 | 8/1997 | Heintz | 15/415.1 |
| 5,691,846 | 11/1997 | Benson, Jr. et al. . | |
| 5,692,263 | 12/1997 | Sorenson | 15/415.1 |
| 5,728,446 | 3/1998 | Johnston et al. . | |
| 5,842,787 | 12/1998 | Kopf-Sill et al. . | |
| 5,885,470 | 3/1999 | Parce et al. . | |
| 5,932,315 | 8/1999 | Lum et al. . | |

FIG.6
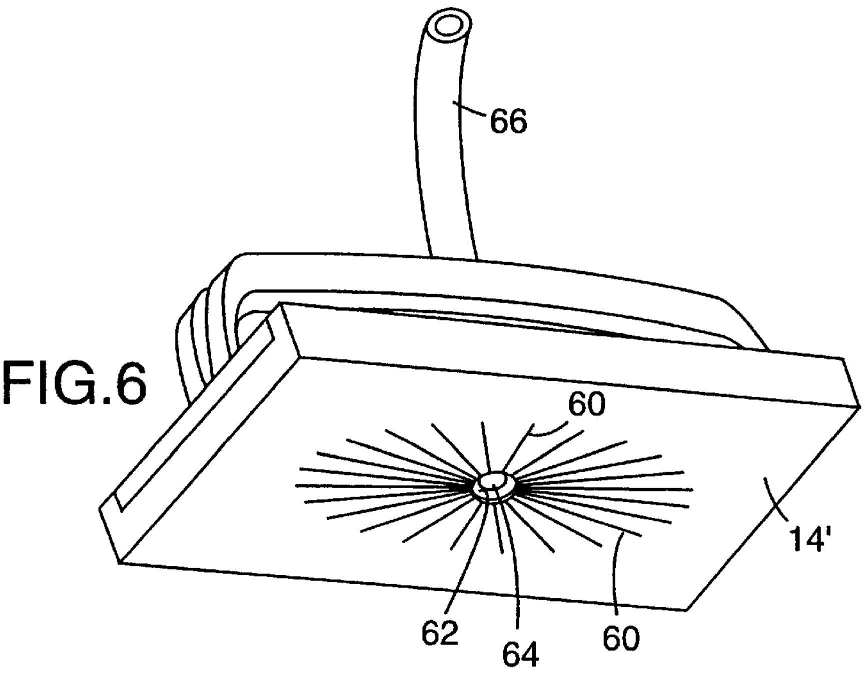
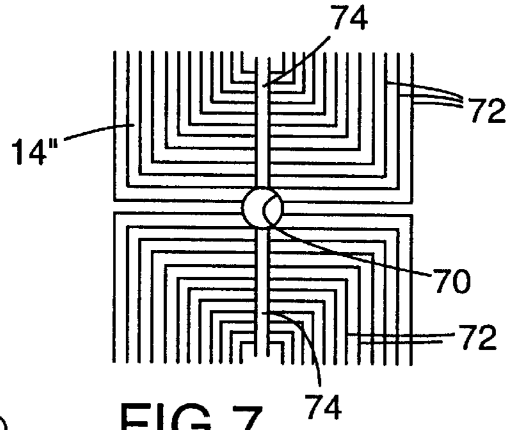
FIG.7
FIG.8
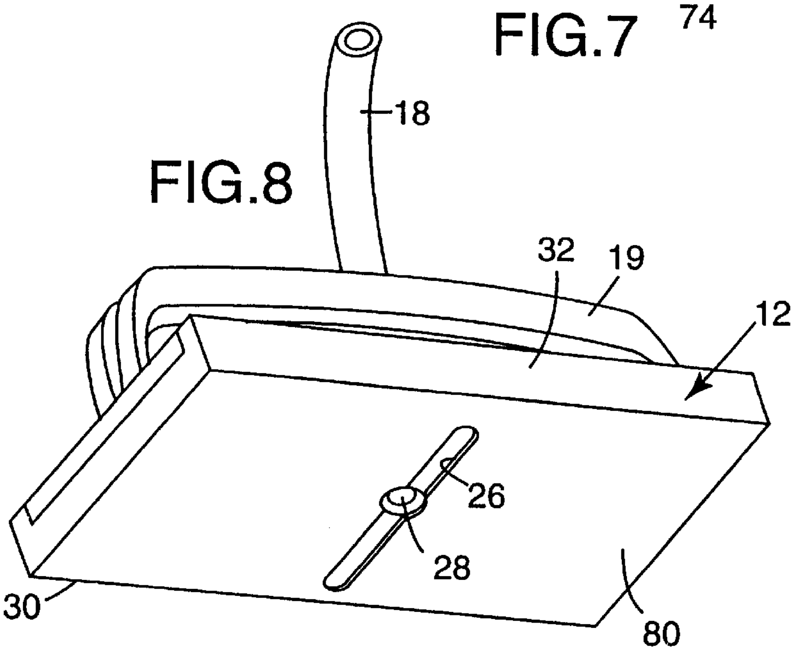

FLUID GUIDE DEVICE HAVING AN OPEN STRUCTURE SURFACE FOR ATTACHEMENT TO A FLUID TRANSPORT SOURCE

The present invention relates to a fluid guide device that includes an open structured surface that defines plural channels with at least some of the channels connected to a fluid transport source, which may provide for fluid suction or supply. Channels of the structured surface can be closed by a surface of an object during use with a fluid transport potential applied to the channels for fluid movement. When suction is applied, the fluid guide device comprises part of a vacuuming system, and when fluid is supplied, the fluid guide device comprises part of an applicator. The present invention is also directed to a method of surface treatment using such a fluid guide device.

BACKGROUND

Many types of vacuuming systems have been developed including those having many different shapes of inlet devices connected with flexible conduits or hoses that are in turn connected with a vacuum generator. Vacuum systems have long been utilized for the purposes of cleaning and removing liquids and/or particulate matter from objects or collection areas. Vacuuming tools associated with vacuum cleaning systems are generally designed based on a desired inlet shape that facilitates cleaning or removal of unwanted matter (liquid or solid) from a particular type of surface. Moreover, such vacuum systems may be otherwise designed (i.e. for flow or power requirements) based upon the application. Typical applications include those for residential or industrial cleaning purposes such as, for example, cleaning walls, carpeting, floors, and furniture, etc. In scientific or industrial operations where debris, excess fluid, or fumes are given off, controlled use of vacuuming technology has been available for removal of the waste at or near the source. Vacuuming tools in the form of nozzles, wands and brushes have been used for the above purposes, and are available in a variety of sizes, shapes, flexibilities and configurations.

A chore in the vacuuming of any surface is that the entire surface typically must be vacuumed. That is, the opening of the vacuuming system inlet device needs to be passed over substantially all of the surface of the object. This becomes more cumbersome for larger surfaces. For example, where a conventional wand is used over a large surface such as a floor or a wall, the job can be quite time consuming. To overcome this, various attachments have been made, such as diverging nozzles, for enlarging the opening of the inlet device so that for a given movement, a larger area is covered. The problem with this approach is that the larger openings also detrimentally affect the suction power of the vacuum system. As the opening size is increased, the suction power is lessened over the area of the opening, or a greater vacuum must be generated. The latter requires bigger motors, for example, and power usage. A similar problem as associated with fluid applicators.

The vacuum removal of liquids is typically accomplished by positioning an inlet device of a vacuuming system within a fluid collection area or by passing the inlet opening over the surface of an area in the manner as above. The latter suffers the same problem discussed above. In the case of the former, the system is effective when the opening of the inlet device is submerged within the collection area. When even a part of the opening is out of the liquid pool, the liquid removal process is substantially ineffective because the suction primarily removes air instead of the collected liquid. Moreover, in addition to the noise of the vacuum generator itself, the suction noise is increased by two-phase fluid flow into and through the system. That is, a mixture of liquid and gas is drawn within the inlet device and through the vacuuming system, and this flow is typically very turbulent and noisy.

The flow of fluid, whether gas or liquid or both, through conduits and nozzles of a fluid transport system having a fluid transport source, can be characterized as active fluid transport. That is, the fluid transport is considered "active" because the fluid transport pertains to a non-spontaneous fluid flow regime that, for the most part, is the result of a force produced by a source external to the transporting device. In the case of a vacuum system, a vacuum generator acts as a source that draws the fluid through the conduits and nozzle of the system. As conventionally used, a vacuum generator can be utilized to simply remove a gas or liquid, or may utilize the fluid flow of gas or liquid for removing solid matter. In the case of an applicator system, a pressure source may be utilized.

Some vacuum systems, particularly for liquid removal, include collection devices that are positionable with respect to other apparatuses for receiving and removing waste matter. Typically, a collector device is designed to accommodate the type of waste matter that is to be collected and its ability to be mounted to the relevant structure. Such collection devices may have an enlarged opening for collecting waste matter from a larger area than the vacuum conduit.

An example of a suction mat designed for use within the surgical field is described in U.S. Pat. No. 4,533,352 to Van Beek et al. A collection device is connected with a vacuum tube so that liquid collected by the device can be removed via the suction tube. The collection device itself includes a rib design for providing controlled drainage of fluid along the collection device and into the suction tube. The ribs additionally provide a supporting function for vessels during a surgical procedure.

Another fluid collection and removal device is disclosed in U.S. Pat. No. 5,437,651 to Todd et al. This device also includes a channeled collection plate, but further comprises an absorbent pad provided over the channeled collection plate. The absorbent pad acts as a fluid collection reservoir.

Other fluid collection devices combined with a vacuum system are disclosed in U.S. Pat. No. 3,520,300 to Flower and U.S. Pat. No. 5,628,735 to Skow. In Flower, an absorbent material is provided over a perforated vacuum body that is further connected with a removal tube. The device of Skow includes a mat comprising a material having a high wicking property and a flexible suction tube that prevents the mat from becoming saturated with fluid. In both cases, the pad or mat acts as the collection device and the vacuum system merely removes the collected fluids.

SUMMARY OF THE INVENTION

The present invention is a fluid guide device that can evenly and effectively distribute the potential forces from a fluid transport source over an area substantially larger than the opening of a source conduit. The fluid guide device includes a first major surface having a structured surface that includes a plurality of flow channels disposed thereon. The flow channels extend from a first point to a second point along the structured surface and have a minimum aspect ratio of about 10:1 and a hydraulic radius no greater than about 300 micrometers ($\mu$m). The fluid guide device also includes an active fluid transport source provided external to the structured polymeric surface to provide a potential over the flow channels to promote movement of matter through the flow channels from a first potential to a second potential. The fluid transport source is connected with a plurality of the flow channels of the structured surface by way of a manifold.

The present invention provides a fluid guide device that can effectively vacuum or apply fluid to a relatively large flat surface area. The term "flat", as used throughout this application, means a surface that has a substantially smooth surface, although not necessarily one that is planar. That is, the surface may be contoured in one or two dimensions, and the contours can be compound as well. The fluid guide device may thus be constructed of a flexible material so that it can easily conform with the flat surface even with contours as contemplated above. The more flexible the fluid guide device, the more its ability to conform to more radical contours. In one construction, the structured surface is provided by a major surface of a layer of polymeric material, such as film, that is mounted to a support body. The structured surface may otherwise be formed directly on a major surface of the support body, or the layer may itself comprise the support body.

A fluid guide device in accordance with the present invention is thus effective as a vacuum inlet for removing particulate matter or the like from a flat surface while covering a greater area of the flat surface with minimized vacuum generation. In particular, such a vacuum inlet can be used to remove small matter such as that found on clean room surfaces. Likewise, for fluid removal, positioning the vacuum inlet device against a flat surface completes an effective fluid guide device. By this, any amount of fluid covered by the vacuum inlet or adjacent any channel opening thereof can be removed. Also, greater quantities of fluid can be evacuated with minimized vacuum source generation.

The present invention has a number of characteristics that impart numerous other advantages into a fluid guide device having a fluid transport source. The fluid guide device makes up a part of an active fluid transport device and has a structured surface that is preferably formed from a polymeric material. The polymeric material allows the channeled structure to be accurately replicated in a relatively inexpensive manner during manufacture. A polymeric layer bearing a microchanneled-structured surface can be readily replicated using a molding or casting technique. The channeled structure thus can be produced without costly processing conditions that would otherwise be entailed when using other techniques such as machining and chemical etching. The use of polymeric materials for forming the structured surface also can allow individual feature fidelities to be maintained in the manufacturing process at relatively high tolerances. Additionally, as above, the polymeric material enables flexible active fluid transport devices to be produced as the fluid guide device.

The provision of discrete flow channels that have a minimum aspect ratio of about 10:1 and a hydraulic radius no greater than about 300 micrometers ($\mu$m) affords microstructured channels that allow the active fluid transport source potential force to be divided amongst numerous channels in a highly distributed manner. Rather than transmit the total potential force through, for example, a single large channel, the potential force can be distributed among a very large number of small channels.

Additionally, a highly-distributed potential force also enables less stress to be placed on items that come in contact with the channels. The use of the microstructured discrete flow channels can allow the potential force from the source to be so highly distributed that minimal stress is placed on the flat surface against which fluid flow occurs.

The microchanneled configuration of a vacuum inlet device of a vacuuming device in accordance with the present invention is also advantageous in that it enables each individual channel to readily acquire fluid from the ambient environment. Furthermore, by providing discrete channels, each discrete channel can acquire fluid independent of one another. One channel can, for example, draw a liquid while its neighboring channel contains only air. In conventional fluid transport devices, where channels are much longer and/or are not discrete, two phase flow of both liquid and air often occurs. The invention's promotion of single-phase flow for liquids also beneficially reduces the stress on the liquid passing through the device and can minimize noise pollution. The invention thus is advantageous in that it is capable of safely and quietly removing liquid from the flat surface.

Also, the small size of the flow channels allows the device to resist relatively high compressive forces without collapse of the flow channels. This advantage enables the fluid guide device to be used in situations where such forces might be present, for example, under heavy loads or when the device is forcefully held against a surface.

BRIEF DESCRIPTION OF THE DRAWINGS

FIG. 6 is a perspective view of a fluid guide device illustrating a channel layout configuration in accordance with the present invention;

FIG. 7 is a top view of a microstructured layer illustrating another channel layout configuration in accordance with the present invention;

FIG. 8 is a perspective view of a fluid guide device illustrating one source and manifold configuration in accordance with the present invention;

DETAILED DESCRIPTION OF THE PREFERRED EMBODIMENTS

Figure 1:
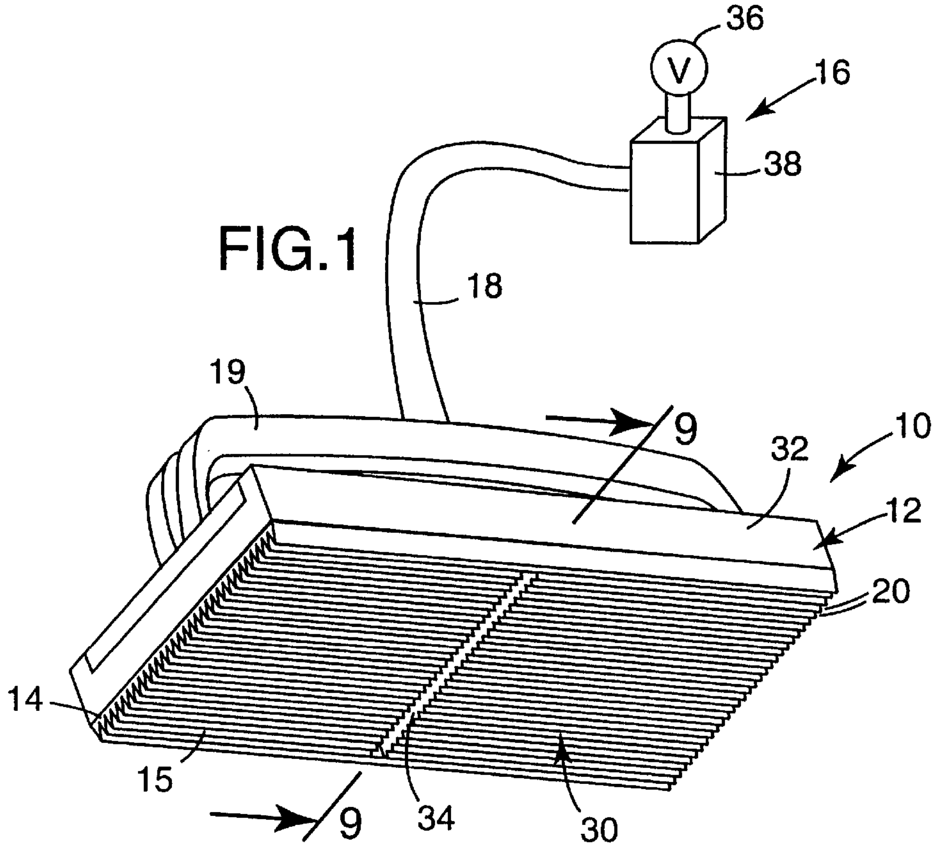
FIG. 1 is a perspective view of a fluid guide device shown schematically connected with a fluid transport source in accordance with the present invention, the fluid guide device including a layer formed with a structured surface mounted to a support body.

With reference to the Figures, like components are labeled with like numerals throughout the several Figures. In FIG. 1, a fluid guide device 10 is illustrated that basically includes a support body 12 and a layer 14 of material that has a structured surface 15 on one of its two major surfaces. The fluid guide device 10 is schematically illustrated connected with a fluid transport source 16 for providing a potential force to assist in moving a fluid over the structured surface 15 of the fluid guide device 10 during use and as described below. A flexible conduit 18 is preferably utilized for connecting the fluid transport source 16 to the structured surface 15 as will be further described below. Preferably, the structured surface 15 is provided within the thickness of the layer 14.

The support body 12 is illustrated in FIG. 1 with a handle 19 that may be provided to permit the fluid guide device 10 to be easily manipulated by a user. The handle 19 may take any number of forms and, if provided, is preferably secured with the support body 12. Handle 19 may be made integrally with the support body 12, or separately attached thereto.

Layer 14 may be comprised of flexible, semi-rigid, or rigid material, which may be chosen depending on the particular application of the fluid guide device 10. The layer 14 preferably comprises a polymeric material because such materials can be accurately formed into a channeled microstructured surface 15. Substantial versatility is available because polymeric materials possess many different properties suitable for various needs. Polymeric materials may be chosen, for example, based on flexibility, rigidity, permeability, etc. The use of a polymeric layer 14 also allows a structured surface to be consistently manufactured with a large number of and high density of fluid flow channels 20. Thus, a highly distributed fluid guide system can be provided that is amenable to being manufactured at a high level of accuracy and economy. It is understood that the layer 14 and its structured surface 15 may comprise plural polymers blended or coextruded to provide constituent parts of the layer 14.

Figure 3:
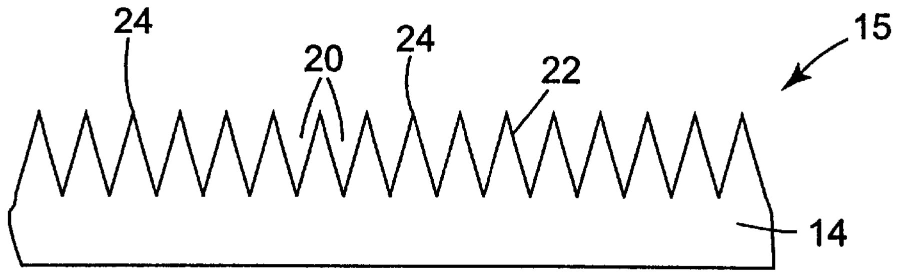
FIG. 3 is an end view of a microstructured layer illustrating one channel configuration in accordance with the present invention.

As shown in FIG. 3, channels 20 can be defined within the layer 14 in accordance with the illustrated embodiment by a series of sidewalls 22 and peaks 24. In some cases, the sidewalls 22 and peaks 24 may extend entirely from one edge of the layer 14 to another (as is shown in FIG. 1), or may extend only along a portion of the structured surface 15. That is, channels 20 that are defined between peaks 24 may extend entirely from one edge to another edge of the layer 14, or such channels 20 may only be defined to extend over a portion of the layer 14. Channels that extend only over a portion of layer 14 may begin at an edge of a layer 14 or may begin and end intermediately within the structured surface 15 of the layer 14.

In order to utilize the fluid guide device 10 against a contacting surface as part of a vacuum system or fluid applying system most effectively, some manner of facilitating fluid flow through channels 20 should be provided. When one or more channels 20 are substantially sealed along their edges, some way to permit fluid flow into those channels 20 facilitates fluid flow within those channels 20. Where the contacting surface is fluid impermeable, it is preferable that each channel 20 opens to at least one side edge of the layer 14 so as to define fluid communication openings from the flow channels 20 to the ambient environment. Such openings may not, however, be desired where the contacting surface permits sufficient fluid flow through it. For example, a porous surface may provide sufficient closure to define the flow channels of the fluid guide device and permit fluid flow into at least some of the channels 20.

Figure 2:
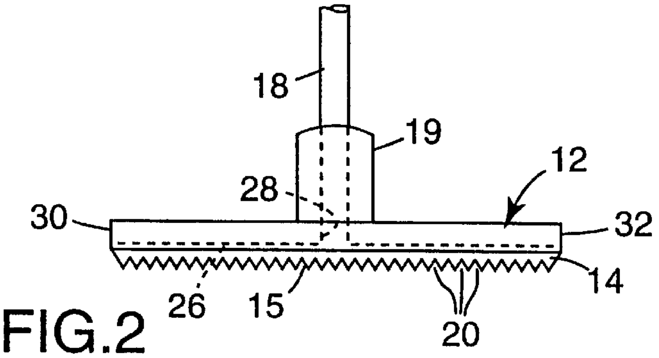
FIG. 2 is a side view of the fluid guide device of FIG. 1 showing a distribution manifold in dashed lines.
Figure 9:
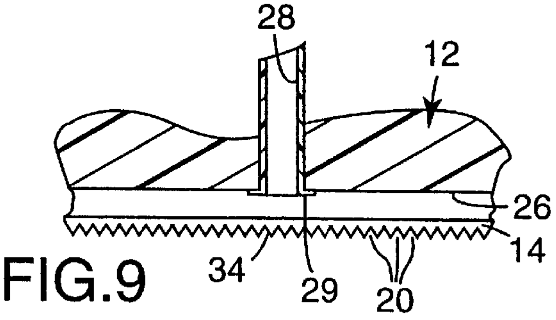
FIG. 9 is a partially broken away cross-sectional view of the fluid guide device of FIG. 1 taken along line 9—9 through the source and manifold of the device.

With reference to FIGS. 1, 2 and 9, a source and manifold system for providing fluid connection between a fluid transport source 16 and the channels 20 is illustrated. A distribution manifold 26 is defined within the support body 12. A source passage 28 also extends through the support body 12 and opens into the distribution manifold 26 for providing a fluid communication between the flexible conduit 18 and the distribution manifold 26. As shown in FIG. 9, the conduit 18 may pass through an opening provided through the support body 12 and be sealingly connected within the distribution manifold 26, such as by an annular flange portion 29. Any conventional or developed manner of providing a fluid connection between a conduit and the manifold 26 are contemplated including, for example, providing a conventional fitting within a passage of the support body 12 that is connectable to a conduit, or integrally making such a fitting with the support body 12.

The distribution manifold 26 can extend substantially completely over the surface of the support body 12 to which the layer 14 is mounted. However, in order to provide some structural support to the layer 14, the distribution manifold 26 is preferably designed to provide the desired flow requirements and to connect to at least some of, but preferably all of, the channels 20 with minimized dimensions. That way, the layer 14 can be connected to the surface of the support body 12 by any conventional or developed technique including permanent mounting techniques as well as releasable and reusable mounting techniques. For example, adhesive may be used as a permanent mount, while removable adhesives or reusable connectors, such as hook and loop connectors, may be used as separable mounts.

In FIG. 8, an example of the support body 12 is illustrated having the distribution manifold 26 provided as a groove extending substantially from a first edge 30 to a second edge 32 of the support body 12. As shown in FIG. 2 in dashed lines, such a distribution manifold 26 can be sufficiently extended to permit fluid communication between the distribution manifold 26 and each of the channels 20 from edge 30 to edge 32.

As shown best in FIG. 1, a slot 34 can be provided for permitting the fluid communication between the distribution manifold 26 and at least a plurality of the channels 20. Each of the channels 20 can be fluidly connected with the distribution manifold 26. To accomplish this, the slot 34 should extend through at least a portion of each of the channels 20 from one edge of layer 14 to another edge of layer 14, these edges preferably being substantially coextensive with the first edge 30 and second edge 32, respectively, of the support body 12. Alternatively, the slot 34 can just as easily be replaced by a series of orifices through the layer 14 permitting communication between at least a plurality of the layers 20 and the distribution manifold 26. An advantage of using separate orifices, is that each channel 20 is selectively connectable to the distribution manifold 26. With this in mind, it is contemplated that plural distribution manifolds may be provided, for example, at different longitudinal points of the support body 12, and the channels may be selectively fluidically connected with any one or more of the distribution manifolds. This may allow, for example, the application of plural different types of liquids at the same time in zones or as a mixture to the surface of an object.

Other types of manifolds are contemplated for connecting a fluid conduit 18 to at least a plurality of the channels 20 so long as this basic functional aspect is provided. A manifold may be connected with plural channels 20 along a side edge of the layer 14, in which case, a support body 12 may not be needed at all. Or, a manifold may be provided to the other major surface of the layer 14 (the one not having structured surface 15) to cover only a slot or the plural openings that communicate with the channels 20. This would basically be a support body 12 that is limited in size to its manifold function.

Like layer 14, and described above, support body 12 or any other functional manifold contemplated in accordance with the present invention can be made of flexible, semi-rigid, or rigid material. The support body 12 may be of a similar or different material as the sheet 14. If a handle 19 is provided, the handle 19 may also be provided of same or different material and have the same or different material properties and characteristics of the support body 12. Moreover, the handle 19 may be provided in any different shape or form based upon the expected application of a particular fluid guide device 10. Where both the sheet 14 and support body 12 are flexible so that the fluid guide device 10 can be easily conformed to a contoured flat surface, it may be desirable to have a handle 19 only attached to the support body 12 at a single location. Of course, a handle need not be provided at all.

The potential source may comprise essentially any means capable of establishing a potential difference across a plurality of the flow channels 20 to encourage fluid movement from a first location to a second location along the flow channels 20. The potential is sufficient to cause, or assist in causing, fluid flow through plural flow channels 20, which is based in part on the fluid characteristics of any particular application. As shown in FIG. 1, the fluid transport source 16 may comprise a generator 36 that is conventionally or otherwise connected to a collector or supply receptacle 38. The generator 36 may comprise, for example, a vacuum generator so that suction can be provided through conduit 18, into distribution manifold 26 through slot 34, and into the flow channels 20. For a pressure application, a pressure generator may be provided for driving fluid from within the receptacle 38 into conduit 18, distribution manifold 26, through slot 34 and discrete flow channels 20.

The fluid guide device 10 of the present invention is specifically designed for use against a flat surface. As used throughout this specification, the term "flat" is not meant to mean planar, but is meant to mean a smooth surface that may be contoured in one or two dimensions, and the contours can be compound as well. More particularly, the fluid guide device 10 is most effective when used against a flat surface that is sufficiently smooth to substantially define discrete flow channels out of the flow channels 20 when the structured surface 15 is positioned against the flat surface. That is, at least a plurality of the flow channels 20 are to be sufficiently closed off by the flat surface so that they will become discrete flow channels with insubstantial fluid mixture or cross-over between adjacent flow channels 20. Where the flat surface is contoured in one or two dimensions, it may be desirable to utilize a flexible fluid guide device 10 so that a plurality of discrete flow channels can be defined during a conformable application.

Where the fluid transport source 16 comprises a vacuum generator 36, suction established within conduit 18 is likewise established within the distribution mantel 26. When at least a plurality of the flow channels 20 are made discrete by application against a flat surface, those discrete flow channels 20 will also have suction established therein along the entire length of those flow channels 20. For placement against an impermeable contacting surface, those flow channels 20 can be open to at least one side edge of the layer 14 so that fluid can be drawn within an opening defined at that edge into the discrete flow channels 20, then through slot 34, within distribution manifold 26, and out of the fluid guide device 10 via conduit 18. When the fluid guide device is used against a contacting surface permitting sufficient fluid flow through it, side edge openings may not be provided. Such a fluid guide device can be used within a vacuum system as a vacuuming system inlet. Such a system is advantageous in that the layer 14 of the fluid guide device 10 can be made substantially larger than the source passage 28 that opens into the distribution manifold 26. By virtue of the fact that the flow channels 20 are preferably microchannels (as defined below), the potential force can be highly distributed while minimizing vacuum generation requirements. That is, a lower suction force can be highly distributed over the entire area of the structured surface 15 to provide a very effective vacuuming tool for covering a substantially large area.

In the case of a pressure generator 36, one or more fluids can be supplied within one or more receptacles 38 through conduit 18, into distribution manifold 26, through slot 34 and into at least a plurality of flow channels 20. During use, the plural flow channels 20 are to be effectively made discrete by contact with a flat surface so that the pressurized fluid can be provided entirely along the flow channels 20. Such a fluid guide device 10 that is connected with a pressure generator 36 may be utilized in any number of systems for treating the flat surface of an object with a liquid or gas in a highly distributed manner with substantially minimized pressure generation requirements.

Other potential sources 16 may be used in the present invention instead of or in conjunction with a vacuum or pressure generator. Generally, any manner of causing fluid flow through the channels 20, is contemplated. That is, any external device or force that encourages fluid transportation through the channels 20 is contemplated. Examples of other potential sources include, but are not limited to, vacuum pumps, pressure pumps and pressure systems, magnetic systems, magneto-hydrodynamic drives, acoustic flow systems, centrifugal spinning, and any other known or later developed fluid drive system utilizing the creation of a potential difference that causes or encourages fluid flow to at least some degree.

Figure 4:
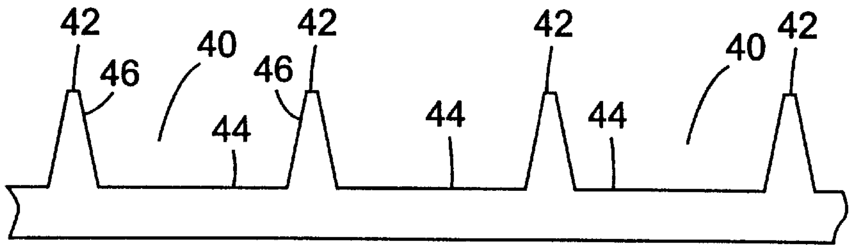
FIG. 4 is an end view of a microstructured layer illustrating another channel configuration in accordance with the present invention.

Although the fluid guide device 10 illustrated in FIGS. 1 and 3 has a structured surface 15 comprising multiple V-shaped peaks 24, other configurations are contemplated. For example, as shown in FIG. 4, channels 40 have a wider, flat valley between slightly flattened peaks 42. These flattened peaks 42 provide a surface to lie against a flat surface of an object during the application of a fluid guide device 10. Bottom surfaces 44 extend between channel sidewalls 46, which is different from the FIG. 3 embodiment where the sidewalls 22 connect together along lines.

Figure 5:
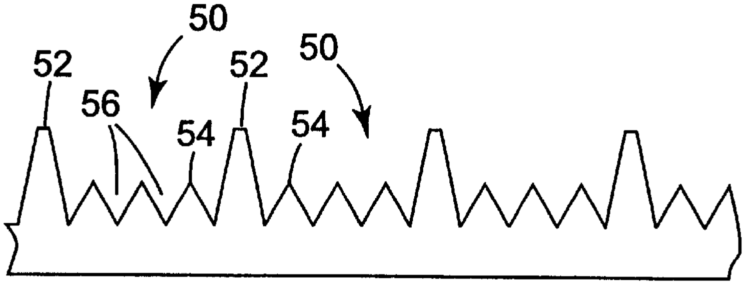
FIG. 5 is an end view of a microstructured layer illustrating yet another channel configuration in accordance with the present invention.

In FIG. 5, a configuration is illustrated where wide channels 50 are defined between peaks 52, but instead of providing a flat surface between channel sidewalls, a plurality of smaller peaks 54 are located between the sidewalls of the peaks 52. These smaller peaks 54 thus define secondary channels 56 therebetween. Peaks 54 may or may not rise to the same level as peaks 52, and as illustrated create a first wide channel 50 including smaller channels 56 distributed therein. The peaks 52 and 54 need not be evenly distributed with respect to themselves or each other. The smaller channels 56 may be beneficial to control fluid flow through the wider channels 50 by modifying frictional forces along the channel's length.

Although FIGS. 1 and 3–5 illustrate elongated, linearly configured channels, the channels may be provided in other configurations. For example, the channels could have varying cross-sectional widths along the channel's length; that is, the channels could diverge and/or converge along the length of the channel. The channel sidewalls could also be contoured rather than being straight in the direction of extension of the channel, or in the channel height. Generally, any channel configuration that can provide at least multiple discrete channel portions that extend from a first point to a second point over the structured surface 15 are contemplated.

In FIGS. 6 and 7, channel configurations are illustrated in plan view that may define a structured surface and a fluid guide device 10 of the present invention. As shown in FIG. 6, a plurality of radially extending channels 60 are provided extending from a central opening 62. As above, for uses in accordance with the present invention, each channel 60 may extend to an edge of the layer 14' for effective fluid transport against a fluid impermeable flat contacting surface. The opening 62 corresponds with a source passage 64 that fluidically connects with conduit 66. In this embodiment, the opening 62 acts as the distribution manifold with the source passage 64. Thus, by modifying the directions of extension of the channels 60, as opposed to the straight channels 20 of FIG. 1, only a small opening 64 is needed to provide the distribution manifold function. Channels 60 need not be linear.

A channel configuration similar in function to that shown in FIG. 6 but designed to more thoroughly cover a given area is illustrated in FIG. 7. Specifically, an opening 70, which like opening 62 provides the distribution manifold function, is provided through layer 14" and connected with a number of U-shaped channels 72 that range from large to small to cover the given area. In this case, feeder channels 74 provide the fluid communication between most of the U-shaped channels 72 and the opening 70. From this, it can be seen that many types of channels are contemplated including the use of primary and secondary channels which may be linear, curved, or compound structures thereof. The U-shaped channels 72 can thus provide openings at the channel ends when such a structured surface is conformed against a flat surface, while the feeder channel 74 may or may not be open at their ends. Generally, any pattern is contemplated in accordance with the present invention as long as a plurality of channels are provided over a portion of the structured surface from a first point to a second point.

In each of the embodiments described above, the structured surface is provided as part of a layer mounted to a manifold or support body. Such a layer may itself comprise the structured surface and the support body. In a similar sense, the support body may have the structured surface provided directly on a major surface thereof, as opposed to having the structured surface provided to the support body by way of a separate layer 14 mounted thereto.

For example, the support body 12 illustrated in FIG. 8 has a major surface 80. In the embodiments above, this major surface 80 is utilized to mount the layer 14 that itself has the structured surface 15. However, the structured surface 15 may be directly formed on this major surface 80. Any of the channel configurations contemplated above with respect to the layer 14 may be applied directly to the support body 12 by conventional or developed techniques. The distribution manifold 26 would thus communicate with the channels formed on the major surface 80 in much the same manner as that described above except for the need of an additional slot 34 through the layer.

As to any of the channels contemplated above and in accordance with the present invention, such channels are defined within a structured layer by the structured surface of a first major surface of the layer. The channels in accordance with the present invention are configured to be microstructured to allow any one channel to fill readily with fluid from the ambient environment independently of the other channels. The microstructured size of each channel encourages single phase flow when liquid is to be transported because it is easy for each channel to receive liquid. Without having air mixed with liquid in the channels, noise generation is significantly reduced and less stress can be placed on liquids that are transported through the fluid guide device when positioned against a flat surface.

The individual flow channels of the microstructured surfaces of the invention are capable of being made substantially discrete by contact with a flat surface. Thus, fluid that enters one flow channel will not, to any significant degree, enter an adjacent channel, although there may be some diffusion between adjacent channels. The channels preferably can independently accommodate the potential relative to one another to direct a fluid along or through a particular channel independent of adjacent channels.

As used here, aspect ratio means the ratio of a channel's length to its hydraulic radius, and hydraulic radius is the wettable cross-sectional area of a channel divided by its wettable channel circumference. The structured surface is a microstructured surface that defines discrete flow channels that have a minimum aspect ratio (length/hydraulic radius) of 10:1, in some embodiments exceeding approximately 100:1, and in other embodiments at least about 1000:1. At the top end, the aspect ratio could be indefinitely high but generally would be less than about 1,000,000:1. The hydraulic radius of a channel is no greater than about 300 $\mu$m. In many embodiments, it can be less than 100 $\mu$m, and may be less than 10 $\mu$m. Although smaller is generally better for many applications (and the hydraulic radius could be submicron in size), the hydraulic radius typically would not be less than 1 $\mu$m for most embodiments. As more fully described below, channels defined within these parameters can provide efficient bulk fluid transport through an active fluid transport device. The structured surface can also be provided with a very low profile.

Thus, active fluid transport devices are contemplated where the structured polymeric layer has a thickness of less than 5000 micrometers, and even possibly less than 1500 micrometers. To do this, the channels may be defined by peaks that have a height of approximately 5 to 1200 micrometers and that have a peak distance of about 10 to 2000 micrometers.

Microstructured surfaces in accordance with the present invention provide flow systems in which the volume of the system is highly distributed. That is, the fluid volume that passes through such flow systems is distributed over a large area. Microstructure channel density from about 10 per lineal cm (25/in) and up to one thousand per lineal cm (2500/in) (measured across the channels) provide for high fluid transport rates.

Figure 10:
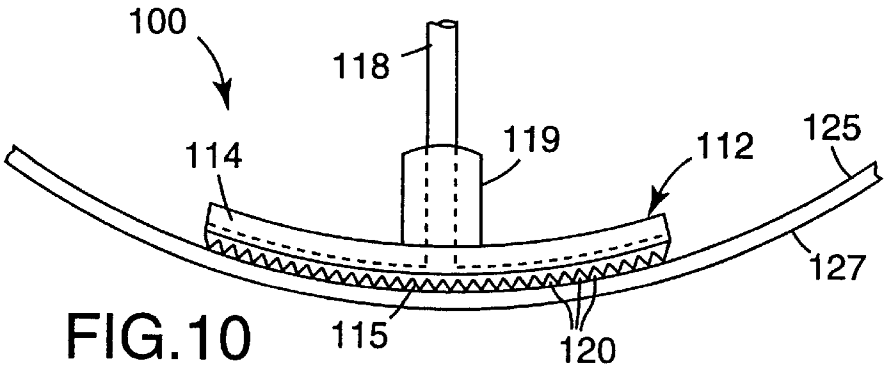
FIG. 10 is a side view of a flexible fluid guide device in accordance with the present invention during application in substantial conformance with the contour of a surface.

With flexible materials, the mechanically flexible nature of such a fluid guide device would allow it to be used in contoured configurations. Flexible devices may be relatively large so that they can be easily handled without breakage and to provide a highly distributed fluid flow over a large area that needs to be affected by the fluid flow through the fluid guide device. A flexible fluid guide device 100 is illustrated in FIG. 10. A flexible support body 112 is provided with a structured surface 115 by way of flexible layer 114. A fluid conduit 118 would communicate with the channels of the structured surface 115 in a manner as described above by way of a distribution manifold. In this case, the channels 120 are illustrated running transversely across the fluid guide device 10, and the handle 119 is positioned so as not to negatively affect the flexible nature of the support body 112 and the layer 114. A distribution manifold should run in the longitudinal direction for this embodiment.

Such a flexible fluid guide device 100 can be conformable to a contoured flat surface 125 of an object 127. As shown, each of the flow channels 120 would be rendered substantially discrete as the support body 112 and layer 114 are made to conform to the shape of surface 125. Although the fluid guide device can be flexible, it can also demonstrate resistance to collapse from loads and kinks. The structured surface provides sufficient structure that can be utilized within any fluid guide device to impart loadbearing integrity for structural support. The small size of the flow channels, as well as their geometry, allows relatively high forces to be applied to the surface without collapsing the flow channels. For example, when the device 100 is conformed to the surface 125 of FIG. 10, the structure permits conformability without detrimentally affecting the size and geometry of the flow channels 120.

The making of structured surfaces, and in particular microstructured surfaces, on a polymeric layer such as a polymeric film are disclosed in U.S. Pat. Nos. 5,069,403 and 5,133,516, both to Marentic et al. Structured layers may also be continuously microreplicated using the principles or steps described in U.S. Pat. No. 5,691,846 to Benson, Jr. et al. Other patents that describe microstructured surfaces include U.S. Pat. No. 5,514,120 to Johnston et al., 5,158,557 to Noreen et al., 5,175,030 to Lu et al., and 4,668,558 to Barber.

Structured polymeric layers produced in accordance with such techniques can be microreplicated. The provision of microreplicated structured layers is beneficial because the surfaces can be mass produced without substantial variation from product-to-product and without using relatively complicated processing techniques. “Microreplication” or “microreplicated” means the production of a microstructured surface through a process where the structured surface features retain an individual feature fidelity during manufacture, from product-to-product, that varies no more than about 50 μm. The microreplicated surfaces preferably are produced such that the structured surface features retain an individual feature fidelity during manufacture, from product-to-product, which varies no more than 25 μm.

Fluid guide layers for any of the embodiments in accordance with the present invention can be formed from a variety of polymers or copolymers including thermoplastic, thermoset, and curable polymers. As used here, thermoplastic, as differentiated from thermoset, refers to a polymer which softens and melts when exposed to heat and re-solidifies when cooled and can be melted and solidified through many cycles. A thermoset polymer, on the other hand, irreversibly solidifies when heated and cooled. A cured polymer system, in which polymer chains are interconnected or crosslinked, can be formed at room temperature through use of chemical agents or ionizing irradiation.

Polymers useful in forming a structured layer in articles of the invention include but are not limited to polyolefins such as polyethylene and polyethylene copolymers, polyvinylidene diflouride (PVDF), and polytetrafluoroethylene (PTFE). Other polymeric materials include acetates, cellulose ethers, polyvinyl alcohols, polysaccharides, polyolefins, polyesters, polyamids, poly(vinyl chloride), polyurethanes, polyureas, polycarbonates, and polystyrene. Fluid guide layers can be cast from curable resin materials such as acrylates or epoxies and cured through free radical pathways promoted chemically, by exposure to heat, UV, or electron beam radiation.

As indicated above, there are applications where flexible fluid guide devices are desired. Flexibility may be imparted to a structured polymeric layer using polymers described in U.S. Pat. Nos. 5,450,235 to Smith et al. and 5,691,846 to Benson, Jr. et al. The whole polymeric layer need not be made from a flexible polymeric material. The main portion, for example, could comprise a flexible polymer, whereas the structured portion or portion thereof could comprise a more rigid polymer. The patents cited in this paragraph describe use of polymers in this fashion to produce flexible products that have microstructured surfaces.

Polymeric materials including polymer blends can be modified through melt blending of plasticizing active agents such as surfactants or antimicrobial agents. Surface modification of the structured surfaces can be accomplished through vapor deposition or covalent grafting of functional moieties using ionizing radiation. Methods and techniques for graftpolymerization of monomers onto polypropylene, for example, by ionizing radiation are disclosed in U.S. Pat. No. 4,950,549 and 5,078,925. The polymers may also contain additives that impart various properties into the polymeric structured layer. For example, plasticisers can be added to decrease elastic modulus to improve flexibility.

Preferred embodiments of the invention may use thin flexible polymer films that have parallel linear topographies as the microstructure-bearing element. For purposes of this invention, a “film” is considered to be a thin (less than 5 mm thick) generally flexible sheet of polymeric material. The economic value in using inexpensive films with highly defined microstructure-bearing film surfaces is great. Flexible films can be used in combination with a wide range of materials for a support body where desired.

Because fluid guide devices of the invention include microstructured channels, the devices commonly employ a multitude of channels per device. As shown in some of the embodiments illustrated above, inventive fluid guide devices can easily possess more than 10 or 100 channels per device. Some applications, the fluid guide device may have more than 1,000 or 10,000 channels per device. The more channels that are connected to an individual potential source allow the potential's effect to be more highly distributed.

The inventive fluid guide devices of the invention may have as many as 10,000 channel inlets per square centimeter of cross section area. Fluid guide devices of the invention may have at least 50 channel inlets per square centimeter. Typical devices can have about 1,000 channel inlets per square centimeter. By having so many channel inlets per unit cross sectioned area, the effect of the potential is so highly distributed at that location of the fluid guide device, that negligible forces may be imparted onto objects that come in contact with the channels.

All of the patents and patent applications cited above are wholly incorporated by reference into this document. Also, this application also wholly incorporates by reference the following patent applications that are commonly owned by the assignee of the subject application and filed on even date herewith: U.S. patent application Ser. No. 09/099,269, to Insley et al. and entitled “Microchanneled Active Fluid Transport Devices”; U.S. patent application Ser. No. 09/106,506, to Insley et al. and entitled “Structured Surface Filtration Media”; U.S. patent application Ser. No. 09/0999,632, to Insley et al. and entitled "Microchanneled Active Fluid Heat Exchanger"; and U.S. patent application Ser. No. 09/100,163, to Insley et al. and entitled "Microstructured Separation Device."

Although the present invention has been described with reference to preferred embodiments, workers skilled in the art will recognize that changes may be made in form and detail without departing from the spirit and scope of the invention.

What is claimed is:

1. A structured surface fluid guide device for distributing a potential from a fluid transport source over an area of a major surface of the fluid guide device and for active fluid transport against a flat surface, the fluid guide device comprising:

(a) a support body having a first major surface provided with a structured surface defining a plurality of substantially discrete flow channels that extend from a first point to a second point along the surface of the support body, the flow channels also having a minimum aspect ratio of about 10:1 and a hydraulic radius no greater than about 300 micrometers;

(b) a fluid transport source external to the structured surface, which source provides a potential over the flow channels to promote movement of matter through the flow channels from a first potential to a second potential; and (c) a manifold connecting the source to the flow channels of the structured surface.

2. The fluid guide device of claim 1, wherein the plurality of discrete flow channels are defined by a series of peaks, each peak having two sidewalls.

3. The fluid guide device of claim 2, wherein the sidewalls of adjacent peaks of the discrete flow channels are separated by a planar floor.

4. The fluid guide device of claim 2, wherein the sidewalls of adjacent peaks of the discrete flow channels are separated by at least one sub-peak, the sub-peak defining a plurality of sub-channels within each discrete flow channel.

5. The fluid guide device of claim 2, wherein the discrete flow channels of a structured surface each comprise a cross-sectional characteristic, the cross-section characteristic of at least a portion of a discrete flow channels varying across the structured surface.

6. The fluid guide device of claim 2, wherein one discrete flow channel of a structured surface is configured differently from another discrete flow channel thereof.

7. The fluid guide device of claim 1, wherein the support body comprises a layer of polymeric material.

8. The fluid guide device of claim 1, wherein the structured surface is provided as a surface of a layer of polymeric material that is mounted to the support body.

9. The fluid guide device of claim 1, wherein the support body is flexible for conforming to contours of an object flat surface.

10. The fluid guide device of claim 1, wherein the structured surface is provided as a surface of a layer of polymeric material that is mounted to the support body, and the manifold comprises a groove formed within a surface of the support body.

11. The fluid guide device of claim 10, wherein the support body comprises a handle and a base, the handle adapted for being held by a user's hand, and the base comprising the manifold and a surface to which the layer of polymeric material is mounted.

12. The fluid guide device of claim 11, wherein the base and the layer of polymeric material are flexible for conforming to the contours of an object flat surface.

13. A method of using a fluid guide device for active fluid transport against a flat surface, said method comprising:

providing a fluid guide device comprising a support body having a first major surface including a structured surface formed thereon, the structured surface defining a plurality of substantially discrete flow channels that extend from a first point to a second point along the surface of the body, the flow channels also having a minimum aspect ratio of about 10:1 and a hydraulic radius no greater than about 300 micrometers, a fluid transport source external to the structured polymeric surface, and a manifold connecting the source to the flow channels of the layer;

positioning the fluid guide device against a flat surface so that a plurality of the discrete flow channels are closed by the flat surface;

generating a potential at the fluid transport source and thereby creating a potential over the flow channels to promote movement of fluid through the flow channels from a first potential to a second potential; and transporting fluid within the flow channels that are closed by the flat surface.

14. The method of claim 13, wherein the providing step further comprises providing a fluid guide device with a flexible support body, and the positioning step further comprises conforming at least a portion of the flexible support body with a portion of the flat surface to close plural flow channels.

15. The method of claim 13, wherein the potential is generated by a vacuum source so that suction is created over the flow channels to promote movement of fluid through the flow channels from a first potential to a second potential.

16. The method of claim 15, wherein the method is used for vacuuming the flat surface by passing the fluid guide device over at least a portion of the flat surface.

17. The method of claim 13, wherein the potential is generated by a pressure source so that fluid flow is promoted through the flow channels from a first potential to a second potential.

18. The method of claim 17, wherein the method is used for applying a fluid to the flat surface by passing the fluid guide device over at least a portion of the flat surface.

* * * * *

UNITED STATES PATENT AND TRADEMARK OFFICE

CERTIFICATE OF CORRECTION

PATENT NO. : 6,080,243
DATED : June 27, 2000
INVENTOR(S) : Thomas I. Insley and Raymond P. Johnston It is certified that error appears in the above-identified patent and that said Letters Patent is hereby corrected as shown below:

Title page,
Item [54], "ATTACHEMENT" should read -- ATTACHMENT --

Item [56], References Cited, under U.S. PATENT DOCUMENTS insert:

| | | |
|---|---|---|
| 3,993,566 | 11/1976 | Goldberg et al. |
| 4,392,362 | 7/1983 | Little |
| 4,413,407 | 11/1983 | Columbus |
| 4,579,555 | 4/1986 | Russo |
| 4,601,861 | 7/1986 | Pricone et al. |
| 4,639,748 | 1/1987 | Drake et al. |
| 4,758,481 | 7/1988 | Fauvel |
| 4,913,858 | 4/1990 | Miekka et al. |
| 5,152,060 | 10/1992 | Schubert et al. |
| 5,176,667 | 1/1993 | DeBring |
| 5,376,252 | 12/27/94 | Ekstrom et al. |
| 5,411,858 | 5/1995 | McGeehan et al. |
| 5,601,678 | 2/1997 | Gerber et al. |
| 5,651,888 | 7/1997 | Shimizu et al. |
| 5,703,633 | 12/1997 | Gehrer et al. |

Item [56] References Cited, under FOREIGN PATENT DOCUMENTS insert:

| | | |
|---|---|---|
| 0 039 291 A1 | 11/1981 | European Pat. Off. |
| 0 329 340 A2 | 8/1989 | European Pat. Off. |
| 32 12 295 A1 | 10/1983 | Germany |
| 195 01 017 A1 | 7/1996 | Germany |
| 1 338 579 | 11/1973 | United Kingdom |
| 1 354 502 | 5/1974 | United Kingdom |
| WO 97/02357 | 1/1997 | WIPO |
| WO 97/13633 | 4/1997 | WIPO |
| WO 98/00231 | 1/1998 | WIPO |
| WO 98/24544 | 6/1998 | WIPO |

UNITED STATES PATENT AND TRADEMARK OFFICE

CERTIFICATE OF CORRECTION

PATENT NO. : 6,080,243
DATED : June 27, 2000
INVENTOR(S) : Thomas I. Insley and Raymond P. Johnston It is certified that error appears in the above-identified patent and that said Letters Patent is hereby corrected as shown below:

<u>Column 1,</u>
Line 57, "as" should read -- is --

Signed and Sealed this

Fourth Day of December, 2001

Attest:

Nicholas P. Godici

Attesting Officer

NICHOLAS P. GODICI
*Acting Director of the United States Patent and Trademark Office*